(12) United States Patent
Fago et al.

(10) Patent No.: US 11,389,175 B2
(45) Date of Patent: Jul. 19, 2022

(54) OCCLUSION CLIP

(71) Applicant: AtriCure, Inc., Mason, OH (US)

(72) Inventors: Frank M. Fago, Mason, OH (US); Kimberly Gray, Florence, KY (US)

(73) Assignee: AtriCure, Inc., Mason, OH (US)

( * ) Notice: Subject to any disclaimer, the term of this patent is extended or adjusted under 35 U.S.C. 154(b) by 0 days.

(21) Appl. No.: 15/868,270

(22) Filed: Jan. 11, 2018

(65) Prior Publication Data

US 2018/0132857 A1 May 17, 2018

Related U.S. Application Data

(63) Continuation of application No. 14/964,930, filed on Dec. 10, 2015, now Pat. No. 9,901,352.

(60) Provisional application No. 62/091,230, filed on Dec. 12, 2014.

(51) Int. Cl.
*A61B 17/122* (2006.01)
*A61B 17/08* (2006.01)
*A61B 17/12* (2006.01)
*A61B 17/00* (2006.01)

(52) U.S. Cl.
CPC .......... *A61B 17/1227* (2013.01); *A61B 17/08* (2013.01); *A61B 17/083* (2013.01); *A61B 17/12* (2013.01); *A61B 17/122* (2013.01); *A61B 2017/00526* (2013.01); *A61B 2017/00884* (2013.01)

(58) Field of Classification Search
CPC ... A61B 17/1227; A61B 17/08; A61B 17/083; A61B 17/12; A61B 17/122
See application file for complete search history.

(56) References Cited

U.S. PATENT DOCUMENTS

| | | | | |
|---|---|---|---|---|
| 1,915,229 A * | 6/1933 | Henry, Jr. | ............... | B21F 45/00 29/243.57 |
| 5,593,414 A * | 1/1997 | Shipp | .................. | A61B 17/1227 606/142 |
| 5,695,505 A * | 12/1997 | Yoon | .................. | A61B 17/0487 606/151 |
| 6,193,732 B1 * | 2/2001 | Frantzen | ............ | A61B 17/1227 606/151 |
| 2005/0021062 A1 * | 1/2005 | Dennis | ............... | A61B 17/1227 606/157 |
| 2005/0277959 A1 * | 12/2005 | Cosgrove | ........... | A61B 17/1285 606/151 |
| 2008/0230971 A1 * | 9/2008 | Farooqui | ................ | B23Q 3/084 269/104 |

(Continued)

*Primary Examiner* — David P Bryant
*Assistant Examiner* — Kyle A Cook
(74) *Attorney, Agent, or Firm* — Dorton & Willis LLP; Ryan Willis (57) ABSTRACT

An occlusion clip comprising: (a) a first elongated occlusion arm; (b) a second elongated occlusion arm; (c) a first elongated biasing arm coupled to a distal portion of the first elongated occlusion arm; (d) a second elongated biasing arm coupled to a distal portion of the second elongated occlusion arm, where a proximal portion of the first elongated biasing arm is coupled to a proximal portion of the second elongated biasing arm, where the first elongated occlusion arm extends parallel to the first elongated bias arm along a majority of its length, and where the second elongated occlusion arm extends parallel to the second elongated bias arm along a majority of its length.

24 Claims, 6 Drawing Sheets

(56) References Cited

U.S. PATENT DOCUMENTS

| | | | | |
|---|---|---|---|---|
| 2011/0029028 A1* | 2/2011 | Peters | ............... | A61N 1/375 607/2 |
| 2014/0058411 A1* | 2/2014 | Soutorine | ............ | A61B 17/122 606/142 |
| 2014/0142597 A1* | 5/2014 | Winkler | ............... | A61B 17/122 606/157 |
| 2014/0259629 A1* | 9/2014 | Dion | ............... | A61F 2/30942 29/558 |
| 2014/0309671 A1* | 10/2014 | Basic | ............... | A61B 17/42 606/158 |

* cited by examiner

FIG. 11

OCCLUSION CLIP

CROSS REFERENCE TO RELATED APPLICATIONS

The present application is a continuation of U.S. Nonprovisional patent application Ser. No. 14/964,930, titled, "OCCLUSION CLIP," filed Dec. 10, 2015, now U.S. Pat. No. 9,901,352, which claims the benefit of U.S. Provisional Patent Application Ser. No. 62/091,230, titled, "OCCLUSION CLIP," filed Dec. 12, 2014, the disclosure of which is incorporated herein by reference.

INTRODUCTION TO THE INVENTION

The present disclosure is directed to occlusion clips and, more specifically, to implantable open-ended occlusion clips. In exemplary form, the exemplary occlusion clips may be utilized to occlude the left atrial appendage.

It is a first aspect of the present invention to provide an occlusion clip comprising: (a) a first elongated occlusion arm; (b) a second elongated occlusion arm; (c) a first elongated biasing arm coupled to a distal portion of the first elongated occlusion arm; (d) a second elongated biasing arm coupled to a distal portion of the second elongated occlusion arm, where a proximal portion of the first elongated biasing arm is coupled to a proximal portion of the second elongated biasing arm, where the first elongated occlusion arm extends parallel to the first elongated bias arm along a majority of its length, and where the second elongated occlusion arm extends parallel to the second elongated bias arm along a majority of its length.

In a more detailed embodiment of the first aspect, the first elongated occlusion arm includes a free proximal end, and the second elongated occlusion arm includes a free proximal end. In yet another more detailed embodiment, the first elongated occlusion arm includes a first convex tissue engaging surface, the second elongated occlusion arm includes a second convex tissue engaging surface, and the first convex tissue engaging surface faces the second convex tissue engaging surface. In a further detailed embodiment, a portion of the first convex tissue engaging surface lies along a first plane, a portion of the second convex tissue engaging surface lies along a second plane, and the first plane and the second plane are parallel to one another. In still a further detailed embodiment, no portion of the first convex tissue engaging surface extends through the second plane, and no portion of the first convex tissue engaging surface extends through the second plane. In a more detailed embodiment, the first elongated occlusion arm includes a first longitudinal length, the second elongated occlusion arm includes a second longitudinal length, more than seventy five percent of the first longitudinal length includes a first gap interposing the first elongated occlusion arm and the first elongated biasing arm, and more than seventy five percent of the second longitudinal length includes a second gap interposing the second elongated occlusion arm and the second elongated biasing arm. In a more detailed embodiment, the first elongated biasing arm includes a third longitudinal length, the second elongated biasing arm includes a fourth longitudinal length, the third longitudinal length is greater than the first longitudinal length, and the fourth longitudinal length is greater than the second longitudinal length.

In yet another more detailed embodiment of the first aspect, the first elongated occlusion arm, the second elongated occlusion arm, the first elongated biasing arm, and the second elongated biasing arm are integral. In yet another more detailed embodiment, the occlusion clip further includes a fabric covering at least a portion of the occlusion clip. In a further detailed embodiment, the fabric covering comprises a tube that concurrently circumscribes at least one of: (a) the first elongated occlusion arm and the first elongated biasing arm; and (b) the second elongated occlusion arm and the second elongated biasing arm. In still a further detailed embodiment, the tube that concurrently circumscribes both: (a) the first elongated occlusion arm and the first elongated biasing arm; and (b) the second elongated occlusion arm and the second elongated biasing arm. In a more detailed embodiment, the occlusion clip includes a first distal cavity interposing a distal end of the first elongated occlusion arm and a distal end of the first elongated biasing arm, and the occlusion clip includes a second distal cavity interposing a distal end of the second elongated occlusion arm and a distal end of the second elongated biasing arm. In a more detailed embodiment, the occlusion clip includes a first proximal cavity interposing a proximal end of the first elongated occlusion arm and a proximal section of the first elongated biasing arm, the occlusion clip includes a second proximal cavity interposing a proximal end of the second elongated occlusion arm and a distal section of the second elongated biasing arm, a first bridge interposes the first proximal cavity and the first distal cavity, the first bridge linking the first elongated occlusion arm and the first elongated biasing arm, and a second bridge interposes the second proximal cavity and the second distal cavity, the second bridge linking the second elongated occlusion arm and the second elongated biasing arm.

It is a second aspect of the present invention to provide an occlusion clip comprising a continuous length of material interposing a pair of terminal ends, the continuous length of material including a first turn having a greater than 150 degree change of direction, a second turn having a second turn having a greater than 150 degree change of direction, a third turn having a greater than 150 degree change of direction, where the third turn occurs at a proximal end of the occlusion clip, where the first and second turns occur proximate a distal end of the occlusion clip, where the proximal end and the distal end are opposite one another, and where the pair of terminal ends occur proximate the proximal end of the occlusion clip.

In a more detailed embodiment of the second aspect, the first, second, and third turns lie within a common plane. In yet another more detailed embodiment, at least two of the first turn, the second turn, and the third turn lie within a common plane. In a further detailed embodiment, the first turn couples a first elongated occlusion arm to a first elongated biasing arm, the second turn couples a second elongated occlusion arm to a second elongated biasing arm, the third turn couples the first elongated biasing arm to the second elongated biasing arm, at least one of the first and second elongated occlusion arms interposes the first and second elongated biasing arms.

It is a third aspect of the present invention to provide a method of fabricating an occlusion clip comprising: (a) cutting out an outline of an occlusion clip precursor from a sheet of material, the occlusion clip precursor including a pair of occlusion arms and a pair of biasing arms; and, (b) compressing the occlusion clip precursor to preload a pair of occlusion arms to form an occlusion clip.

In a more detailed embodiment of the third aspect, the step of cutting out the outline is performed using electrical discharge machining. In yet another more detailed embodiment, the electrical discharge machining includes wire electrical discharge machining. In a further detailed embodiment, the method further includes wrapping the occlusion clip in a fabric. In still a further detailed embodiment, the fabric comprises a fabric tube that promotes tissue ingrowth. In a more detailed embodiment, the occlusion clip comprises a continuous length of material interposing a pair of terminal ends, the continuous length of material including a first turn having a greater than 150 degree change of direction, a second turn having a second turn having a greater than 150 degree change of direction, a third turn having a greater than 150 degree change of direction, where the third turn occurs at a proximal end of the occlusion clip, where the first and second turns occur proximate a distal end of the occlusion clip, where the proximal end and the distal end are opposite one another, and where the pair of terminal ends occur proximate the proximal end of the occlusion clip.

DETAILED DESCRIPTION

The exemplary embodiments of the present disclosure are described and illustrated below to encompass various aspects of implantable open-ended occlusion clips and methods of implanting open-ended occlusion clips to occlude the left atrial appendage. Of course, it will be apparent to those of ordinary skill in the art that the embodiments discussed below are exemplary in nature and may be reconfigured without departing from the scope and spirit of the present disclosure. However, for clarity and precision, the exemplary embodiments as discussed below may include optional steps, methods, and features that one of ordinary skill should recognize as not being a requisite to fall within the scope of the present disclosure.

Referencing FIGS. 1-4, a first exemplary occlusion clip 100 that may be used to occlude a left atrial appendage comprises a unitary body that may be fabricated from titanium using titanium sheet stock. A more detailed description of the process utilized to fabricate this first exemplary occlusion clip 100 will be discussed in a later section.

By way of an exemplary coordinate system, a thickness of the exemplary occlusion clip is taken along a Z-axis. Perpendicular to this Z-axis is a Y-axis and an X-axis (that is also perpendicular to the Y-axis). In exemplary form, the height of the occlusion clip 100 is taken along the Y-axis, while a longitudinal length (dominant dimension) of the occlusion clip 100 is taken along the X-axis.

In exemplary form, the occlusion clip 100 includes a U-shaped section 110 that is integrally coupled to a pair of elongated biasing/spring arms 120, 130. Each elongated biasing arm 120, 130 is integrally coupled to its own elongated occlusion arm 140, 150 that extends toward the U-shaped section 110. In particular, the U-shaped section 110 comprises a first turn 112 having a change of direction between approximately 145 to 215 degrees measured between the pair of elongated biasing arms 120, 130. Moreover, the transition between the first elongated biasing arm 120 and the first elongated occlusion arm 140 comprises a second turn 114 having a change of direction between approximately 145 to 215 degrees measured between the first elongated biasing arm 120 and the first elongated occlusion arm 140. Similarly, the transition between the second elongated biasing arm 130 and the second elongated occlusion arm 150 comprises a third turn 116 having a change of direction between approximately 145 to 215 degrees measured between the second elongated biasing arm 130 and the second elongated occlusion arm 150.

Each elongated occlusion arm 140, 150 is substantially rigid (i.e., inflexible) and includes a terminal end 160, with the terminal ends comprising the beginning and end of a course of material constituting the exemplary occlusion clip 100. In this exemplary embodiment, each occlusion arm 140, 150 includes a tissue engaging surface 180 that is convex. In exemplary form, the convex nature of the tissue engaging surface 180 is substantially constant along a longitudinal length (dominant dimension along the X-axis) of a respective occlusion arm 140, 150. More specifically, the profile of the tissue engaging surface 180 embodies an arc of a circle.

Interposing the tissue engaging surface 180 is a pair of planar surfaces 210 that are uniformly spaced apart from one another. For purposes of explanation with respect to this first exemplary embodiment, the thickness of titanium material (in the Z-direction) comprising the U-shaped section 110, the elongated biasing arms 120, 130, and the elongated occlusion arms 140, 150 (but for the tissue engaging surfaces 180) is constant. The arcuate profile of the tissue engaging surfaces 180 decreases the thickness of the occlusion clip 100 (in the Z-direction) until reaching zero at an apex 230. In other words, the apex 230 of each tissue engaging surface 180 occurs midway along a thickness dimension of the occlusion clip (i.e., in the Z-direction, midway between the planar surfaces 210) so that in the closed position (shown in FIG. 4) the tissue engaging surfaces 180 are parallel to one another and the apexes contact one another or are spaced apart from one another a uniform distance.

Each planar surface 210 defines a respective opposing lateral boundary of the occlusion clip 100. In this exemplary embodiment, the height of the planar surfaces 210 partially outlining the U-shaped section 110 (taken normal to the outer peripheral surface 260 is the interior surface 300) at the apex is approximately twenty-five percent (25%) greater than the height of the elongated biasing arms 120, 130 (taken normal to the outer peripheral surface 260 is the interior surface 320), which is substantially constant along the longitudinal length of the elongated biasing arms until proximate the turns 114, 116. This twenty-five percent (25%) increase in height decreases linearly until reaching zero percent change where the U-shaped section 110 meets the linear elongated biasing arms 120, 130. At the second and third turns 114, 116, the height of the planar surface 210 is maximized. In other words, the height of the planar surface 210 at the end of the turns 114, 116 is approximately equal to the height of the elongated biasing arms 120, 130, in addition to the height of the occlusion arms 140, 150, in addition to the height of a gap 240 between the elongated biasing arms 120, 130 and the occlusion arms 140, 150. This maximum height of the planar surfaces 210 decreases abruptly when extending proximally along the elongated occlusion arms 140, 150. In particular, the height of the planar surfaces 210 decreases linearly along the length of the elongated occlusion arms 140, 150 until reaching a minimum height proximate the terminal end 160. In contrast, when moving distally, the maximum height of the planar surfaces 210 decreases slightly until reaching a distal end 250. Proximate the distal end 250, the height of the planar surfaces 210 decreases and the profile changes embodying the curvature of a circle until reaching the distal end.

The distal end 250 is partially defined by an outer peripheral surface 260 that interposes the planar surfaces 210. In exemplary form, the height of this peripheral surface 260 is constant (in the Z-direction), consistent with the constant thickness of the clip 100. At the distal end, the peripheral surface 260 is planar, but takes on an arcuate curvature that tracks the circle curvature of the planar surfaces. This arcuate curvature leads into a planar distal segment 270 is joined to a planar proximal segment 280 near the second and third turns 114, 116. The proximal planar segment 280 joins a curved section 290, the curvature of which changes depending upon whether the clip 100 is in an open or closed position. Opposite the outer peripheral surface 260 is an interior surface 300.

The interior surface 300 cooperates with the planar surfaces 210, the outer peripheral surface 260, and the tissue engaging surfaces 180 to delineate the exterior boundary surfaces of the clip 100. In particular, the interior surface 300 includes a curved section 310, the curvature of which changes depending upon whether the clip 100 is in an open or closed position. This curved section 310 transitions into a pair of elongated planar biasing arm sections 320 that respectively join U-shaped curves 330, one for each turn 114, 116. Each U-shaped curve 330 is also joined to a respective elongated planar occlusion arm section 340. Two terminal ends 160 of the elongated biasing arms 120, 130 are delineated by corresponding blunt surfaces that include a rounded-over portion 350 that transition into a respective elongated planar occlusion arm section 340.

Figure 1:
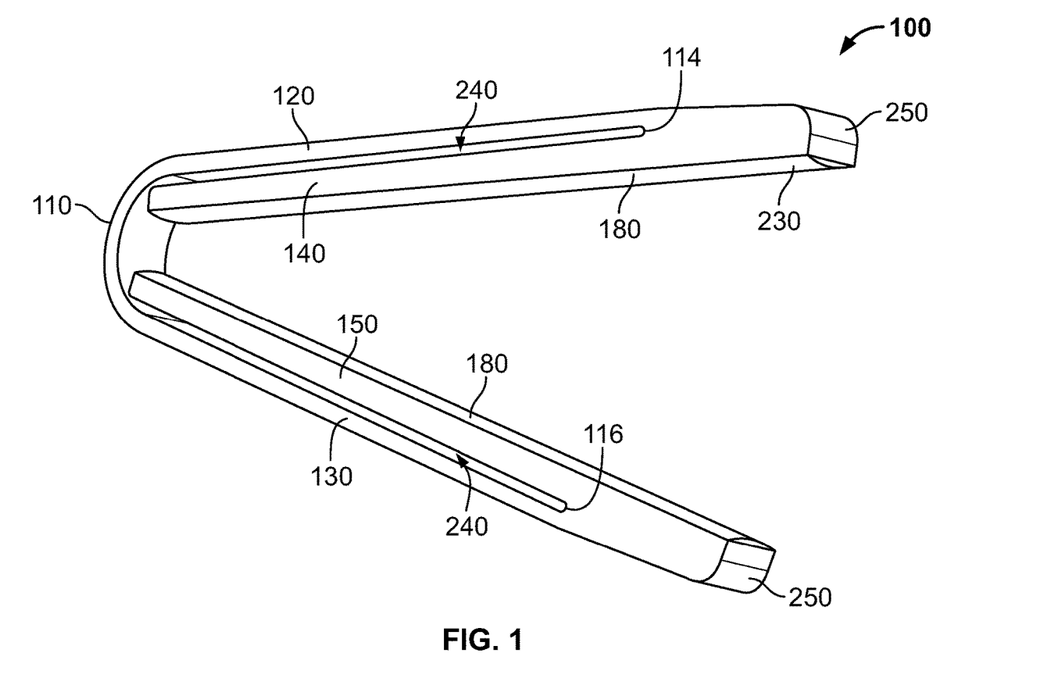
FIG. 1 is an elevated perspective view of a first exemplary occlusion clip in accordance with the instant disclosure shown in an open position.
Figure 2:
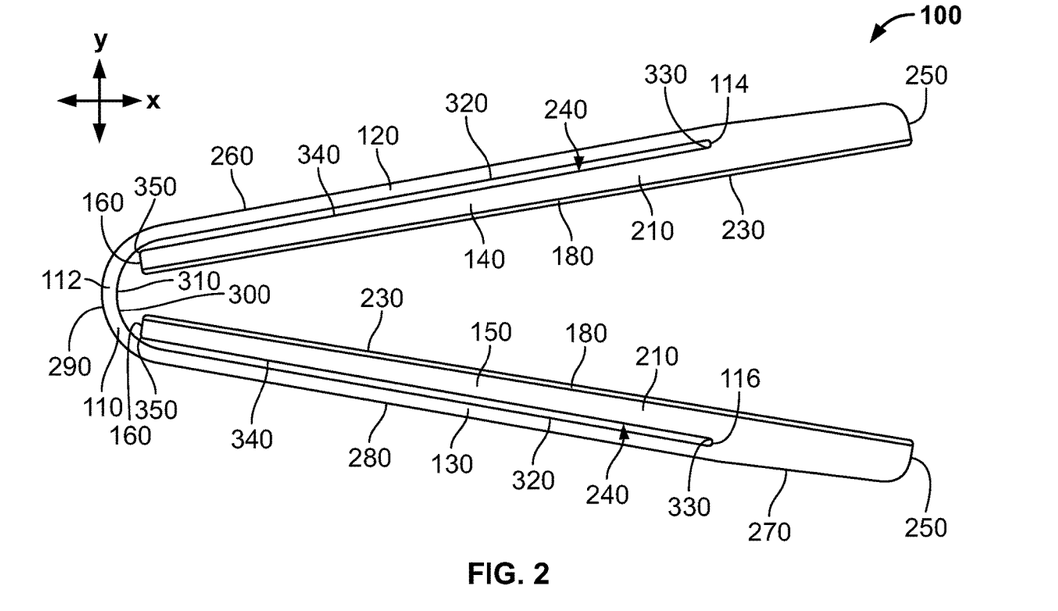
FIG. 2 is a profile view of the first exemplary occlusion clip of FIG. 1 shown in an open position.
Figure 3:
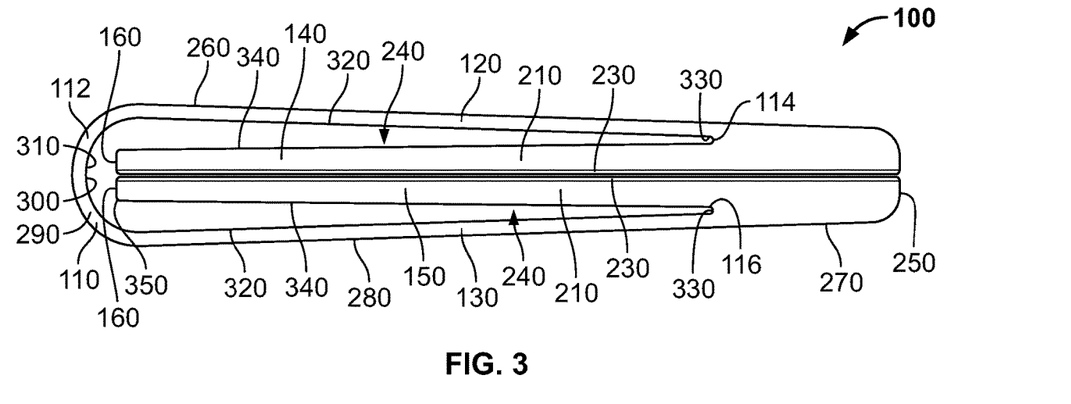
FIG. 3 is a profile view of the first exemplary occlusion clip of FIG. 1 shown in a closed position.
Figure 4:
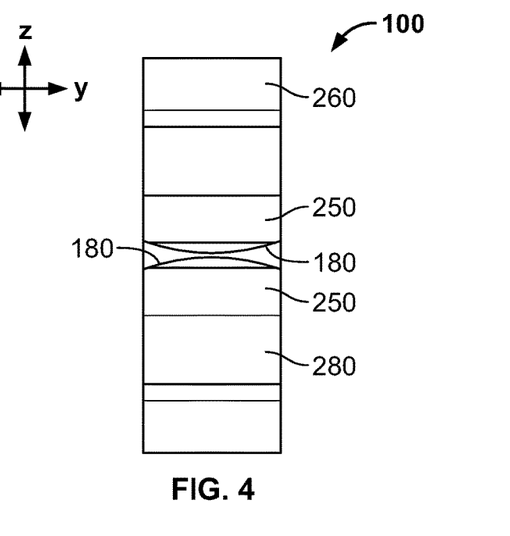
FIG. 4 is an end view of the first exemplary occlusion clip of FIG. 1 shown in a closed position.

As shown in FIGS. 3 and 4, the clip 100 takes on a closed position when nothing interposes the elongated biasing arms 120, 130. In this closed position, the elongated biasing arms 120, 130 abut one another. More specifically, the tissue engaging surfaces 180 are minimally spaced apart or contact one another. In addition, the gap 240 between the elongated biasing arms 120, 130 and the occlusion arms 140, 150 is more pronounced toward the U-shaped section 110. In other words, the elongated biasing arms 120, 130 are not parallel to the occlusion arms 140, 150. But this is not necessarily the case when the clip 100 takes on an open position.

Referring back to FIGS. 1-4, any position beyond the closed position is generally referred to as an open position. For purposes of discussion, and depicted in exemplary form, the fully open position corresponds to the elongated biasing arms 120, 130 oriented in parallel to the occlusion arms 140, 150, but the spacing (i.e., gap 240 width) between the distal portions of the proximal portions of the occlusion arms 140, 150 (proximate the second and third turns 114, 116) is several multiples of the spacing between the proximal portions of the occlusion arms 140, 150 (proximate the terminal ends 160). In this fully open position, the clip 100 may be configured to receive a left atrial appendage (LAA) in between the tissue engaging surfaces 180. More specifically, when in the fully open position, the clip 100 is moved along the base of the LAA (parallel with the dominant dimension of the LAA base) so that the LAA can be captured between the tissue engaging surfaces 180 without going over the top of the LAA. It should be noted that the elongated biasing arms 120, 130 have an aspect ratio that is thinner in the Y-direction to allow for bending of the arms in the Y-direction, but is thicker in the Z-direction to retard the distal ends 250 of the clip 100 from separating in the Z-direction.

Figure 5:
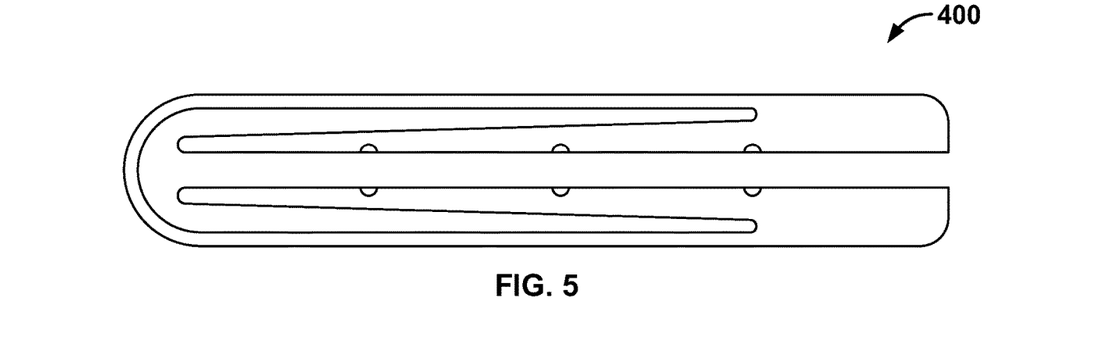
FIG. 5 is a profile view of a precursor to the first exemplary occlusion clip of FIG. 1.
Figure 6:
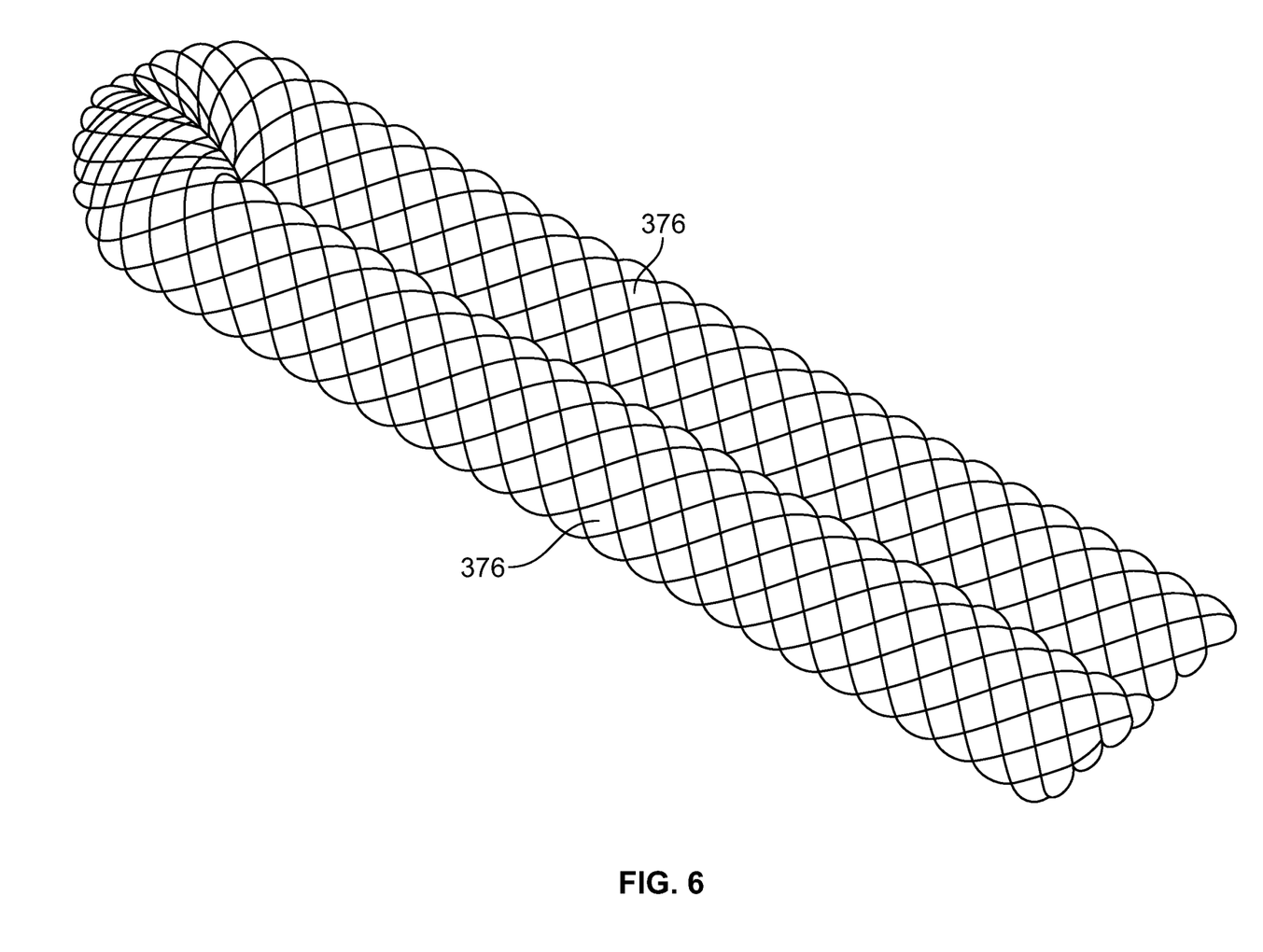
FIG. 6 is an elevated perspective view of the first exemplary occlusion clip of FIG. 1 shown in a closed position and covered by a fabric tube.

Referring to FIGS. 5 and 6, the exemplary clip 100 may be fabricated in various ways. By way of example, the exemplary clip 100 fabrication will be discussed in the context of wire electrical discharge machining (WEDM). In exemplary form, two or more sheets of an implantable grade titanium material (e.g. grade 2, grade 5), with each sheet having a thickness dimension of ⅛ inch and having length and width dimensions (e.g., 12 inch×12 inch, 18 inch×12 inch, etc.), are stacked upon one another along the thickness dimension and submerged within a dielectric bath, which may comprise deionized water. By way of example, the stacked sheets of titanium comprise a first electrode and the wire electrical discharge machine includes a second electrode comprising a spooled material (e.g., brass wire). Those skilled in the art are familiar with WEDM and, accordingly, a detailed description of WEDM has been omitted in furtherance of brevity.

Using WEDM, the outline of a precursor to the exemplary clip 100 shown in FIG. 5 is concurrently cut through each of the titanium sheets, thereby fabricating concurrently the same number of clips as there are sheets. After the outline of the precursor is cut, the wire electrical discharge machine repositions the second electrode with respect to the titanium sheets to form the outline of another precursor at locations previously uncut. This process is repeated until the wire electrical discharge machine exhausts the uncut locations where the exemplary precursor can be cut.

Subsequent to WEDM, each precursor clip (which all have the same shape and dimensions) is subjected to a tissue engaging surface step. In exemplary form, the tissue engaging surface step machines away material from the occlusion arms 140, 150 (that previously had a block C-shaped profile; i.e. rectangular profile) to form the arcuate profile of the tissue engaging surfaces 180.

Subsequent to the tissue engaging surface step, each precursor clip (which all have the same shape and dimensions) is subjected to a compression step. In exemplary form, the compression step establishes the dimension of any gap interposing the tissue engaging surface 180, as well as any preload (i.e., the amount of force required to separate the tissue engaging surfaces from one another presuming no gap is present between the tissue engaging surfaces post compression step) exhibited by the clip 100. In this exemplary process, the precursor is compressed proximate the U-shaped section 110, which causes the tissue engaging surfaces 180 to move toward one another. For example, the U-shaped section may be compressed approximately 0.38 inches, which results in zero gap between the tissue engaging surfaces 180 and a preload of approximately 1.5 pounds of force (i.e., 1.5 pounds of force or greater is required to separate the engaging surfaces 180 from one another). The compression step results in a closing force on the occlusion arms 140, 150 that is essentially constant from the distal to the proximal end especially between the fully closed position and an open position exhibiting a four millimeter opening/gap. In this fashion, the elongated biasing arms 120, 130 are substantially elastic, but the U-shaped section 110 is substantially non-elastically deformed. Moreover, depending upon the length of the clip 100 (in the X-direction), the amount of force required to open the clip may change. In a circumstance where the target force at two millimeters of opening/gap between the occlusion arms 140, 150 approximately 0.032 pounds per millimeter of occlusion member length, this may result in different amounts of clamping force applied to the U-shaped section 110 of the clip 100 depending upon its length. For example, in the context of a fifty millimeter clip 100, the compression may impart a preload of approximately 1.6 pounds, whereas in the context of a thirty-five millimeter clip the preload may be reduced to 1.12 pounds (where a greater pound preload requires a greater extent of compression). After the precursor is compressed proximate the U-shaped section 110, the exemplary clip 100 fabrication is complete and the clip components take on the preloaded positions shown in FIGS. 3 and 4.

In this first exemplary embodiment, the clip 100 may exhibit a uniform force across the length of the occlusion arms 140, 150. In particular, the uniform force may be applied across the length of the occlusion arms 140, 150 between one to four millimeters opening, for example. This uniform force profile along the length of the occlusion arms 140, 150 coincides with common compressed thicknesses of a majority of left atrial appendages. For example, data has shown that a compressed left atrial appendage, sufficient to occlude without severing, has a thickness on the order to of two millimeters, plus-or-minus one millimeter. Accordingly, a clip exerting a uniform force profile within a range of one to four millimeters would encompass a majority of patient left atrial appendages subjected to occlusion compression. To the extent that uniform force is not exactly obtainable across the length of the occlusion arms 140, 150, it should be noted that the clip 100 may be preloaded to more heavily toward the distal end 250 of the clip to encourage tissue clamped between the occlusion arms from squeezing out beyond the distal end.

As shown in FIG. 6, in further exemplary form, the exemplary clip 100 may be encapsulated using a fabric tube 376 that may be fabricated from any of various materials operative to allow biologic tissue ingrowth such as, without limitation, polyethylene terephthalate and expanded polytetrafluoroethylene. In particular, the fabric tube 376 may be treated with collagen, albumin, etc., to promote tissue ingrowth. In this exemplary embodiment, a passage extends through the fabric tube, with opposing openings at the ends of the tube demarcating the beginning and end respectively of the passage. By way of example, one opening of the fabric tube 376 circumscribes one of the distal ends 250 of the clip 100 and is moved proximally along the length of the elongated biasing arm 120 and the elongated occlusion arm 140 to circumscribe both concurrently. Continued proximal movement of the fabric tube 376 eventually reaches the terminal end 160 of the elongated occlusion arm 140 and the U-shaped section 110, where the fabric tube follows the shape of the U-shaped section 110 and reaches the terminal end 160 of the elongated occlusion arm 150. At this point, the opening of the fabric tube 376 is repositioned distally to concurrently circumscribe the elongated biasing arm 130 and the elongated occlusion arm 150. Continued distal movement of the fabric tube 376 eventually results in the end of the fabric tube passing slightly beyond the distal end 250 of the elongated biasing arm 130 and the elongated occlusion arm 150, whereby the entire clip is housed within the passage of the fabric tube. The fabric tube 376 includes corresponding ends that extend beyond the distal ends 250 of the occlusion clip 100 a sufficient length to allow the corresponding ends to be sewn shut. The ends may be sewn shut after the fabric tube 376 has been positioned around the clip 100, or one end of the fabric tube may be sewn shut prior to positioning the fabric tube around the clip. Nevertheless, after the fabric tube 376 has been positioned around the clip 100, the sewn ends of the fabric tube operate enclose the clip within the fabric tube.

Figure 7:
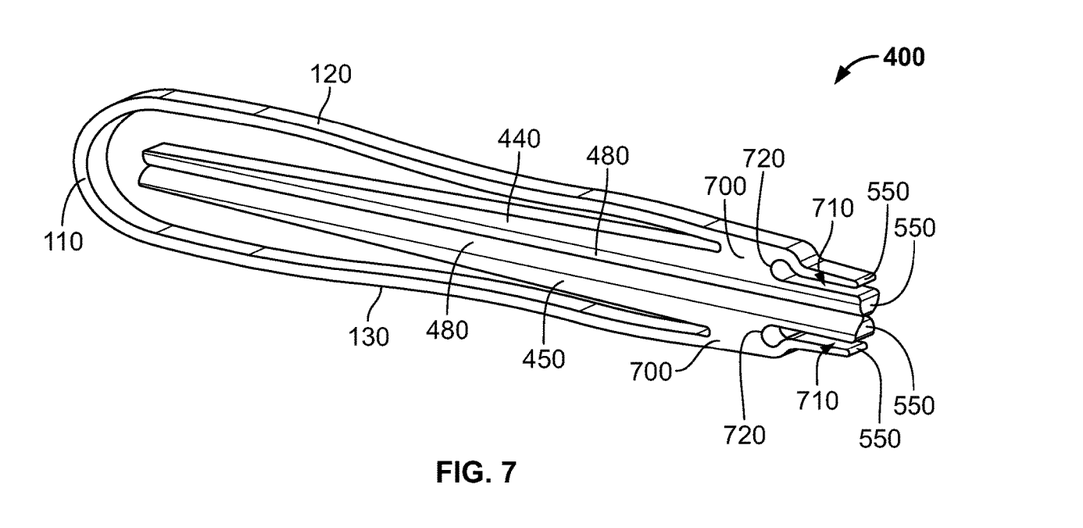
FIG. 7 is an elevated perspective view of a second exemplary occlusion clip in accordance with the instant disclosure shown in a closed position.
Figure 8:
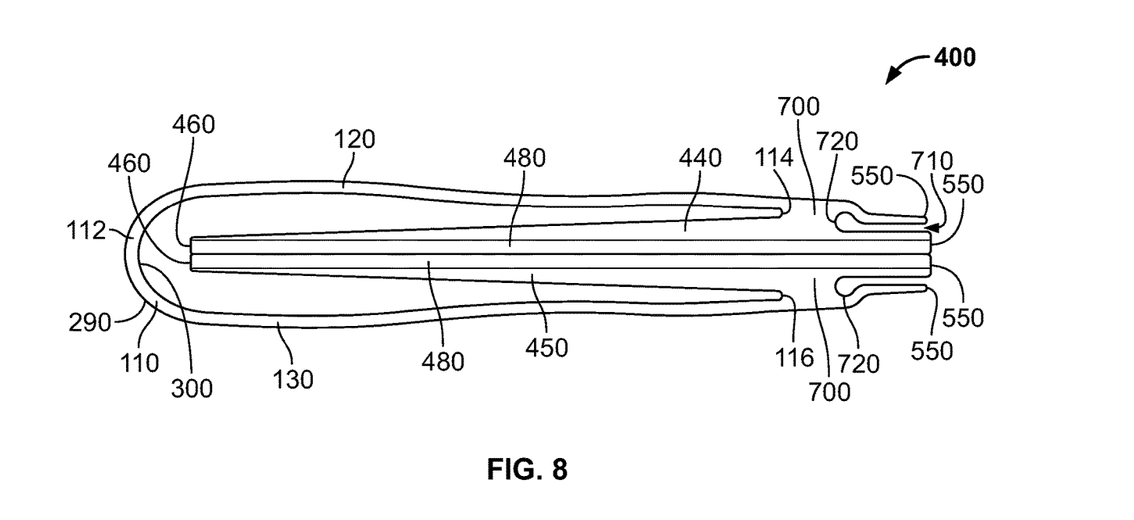
FIG. 8 is a profile view of the second exemplary occlusion clip of FIG. 7 shown in a closed position.
Figure 9:
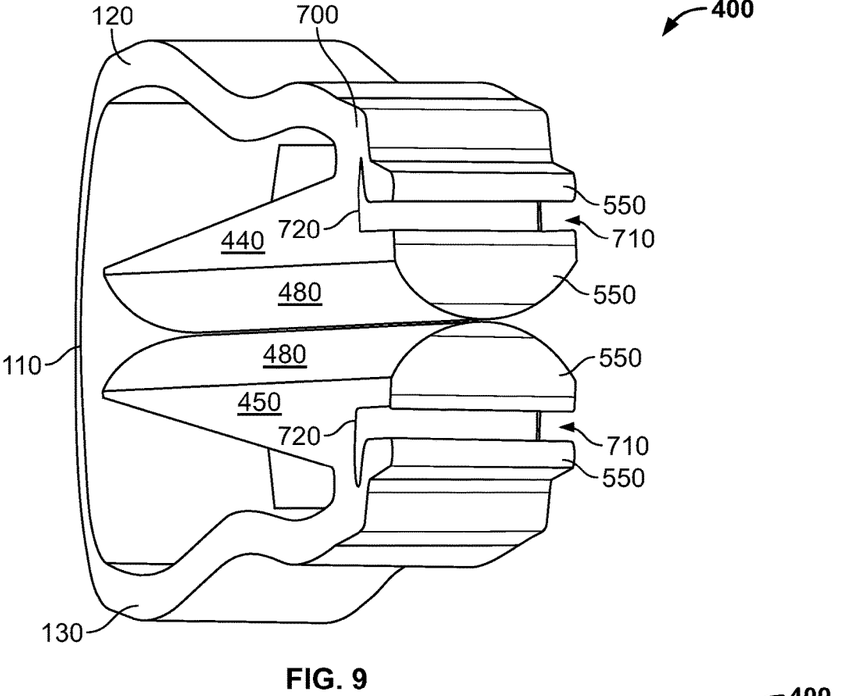
FIG. 9 is a perspective end view of the second exemplary occlusion clip of FIG. 7 shown in a closed position.

Referencing FIGS. 7-9, a second exemplary occlusion clip 400 also comprises a unitary body that may be fabricated from titanium using titanium sheet stock. As will be discussed in more detail hereafter, this second exemplary occlusion clip 400 may be fabricated in a similar manner to the first exemplary occlusion clip 100.

For purposes of explanation, this second exemplary occlusion clip 400 has many features that are in common with the first exemplary occlusion clip 100. Consequently, a detailed discussion of these common features has been omitted in furtherance of brevity, but will be apparent from the common reference numerals present in the accompanying drawings for this second exemplary occlusion clip 400.

This second exemplary occlusion clip 400 differs in part from the first exemplary occlusion clip 100 by having occlusion arms 440, 450 that do not have a uniform height between a proximal end 460 and the second turn 114 or third turn 116. Instead, the height (in the Y-direction) of the occlusion arms 440, 450 decreases linearly in a proximal direction from the second/third turn 114/116 until reaching the proximal end 460.

In addition, the second exemplary occlusion clip 400 differs from the first exemplary occlusion clip 100 by having tissue engaging surfaces 480 with a different arcuate profile. In exemplary form, the tissue engaging surfaces 480 have an arcuate profile that corresponds to the arc of a circle having a substantially smaller diameter than the arcuate profile of the tissue engaging surfaces 180 that corresponds to the arc of a circle having a much larger diameter. In this fashion, the height (in the Y-direction) of the tissue engaging surfaces 480 is substantially greater than that of the tissue engaging surfaces 180 of the first exemplary clip 100.

Figure 10:
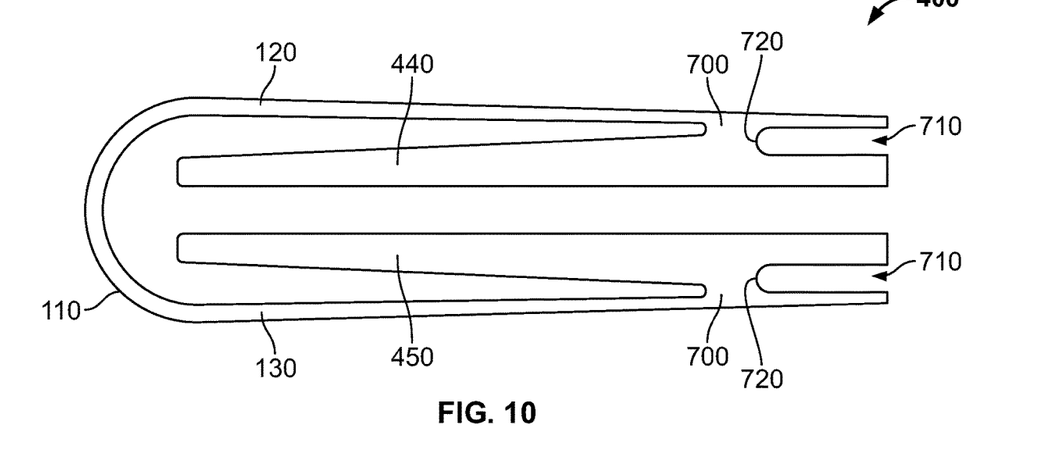
FIG. 10 is a profile view of a precursor to the second exemplary occlusion clip of FIG. 7.

Yet another distinction between the second exemplary occlusion clip 400 and the first exemplary occlusion clip 100 is the distal ends 250, 550. Initially, as shown in FIG. 10, the distal ends 550 of the occlusion clip 400 precursor each include a U-shaped recess 710 that operates to divide the distal ends of the elongated biasing arms 120, 130 from the distal ends of the occlusion arms 440, 450 so that a bridge portion 700 connects a respective elongated biasing arm 120, 130 to a respective occlusion arm 440, 450. In exemplary form, the height of the U-shaped recess 710 in the occlusion clip 400 precursor is substantially constant and tapers at a distal end 720 until reaching zero, indicative of the U-shaped profile.

Similar to the first exemplary occlusion clip 100, this second exemplary occlusion clip may also be fabricated using WEDM. In exemplary form, two or more sheets of an implantable grade titanium material (e.g. grade 2, grade 5), with each sheet having a thickness dimension of ⅛ inch and having length and width dimensions (e.g., 12 inch×12 inch, 18 inch×12 inch, etc.), are stacked upon one another along the thickness dimension and submerged within a dielectric bath, which may comprise deionized water. By way of example, the stacked sheets of titanium comprise a first electrode and the wire electrical discharge machine includes a second electrode comprising a spooled material (e.g., brass wire). Using WEDM, the outline of a precursor to the exemplary clip 400 shown in FIG. 10 is concurrently cut through each of the titanium sheets, thereby fabricating concurrently the same number of clips as there are sheets. After the outline of the precursor is cut, the wire electrical discharge machine repositions the second electrode with respect to the titanium sheets to form the outline of another precursor at locations previously uncut. This process is repeated until the wire electrical discharge machine exhausts the uncut locations where the exemplary precursor can be cut.

Subsequent to WEDM, each precursor clip (which all have the same shape and dimensions) is subjected to a crimping step. In exemplary form, the distal ends 550 of the elongated biasing arms 120, 130 and the occlusion arms 440, 450 are crimped to deform the distal end of each elongated biasing arms 120, 130. As shown in FIGS. 7-9, the result of the crimping step is deformation of the elongated biasing arms 120, 130 to reduce the height of the U-shaped recess 710, with the exception of the proximal end 720. Though not required, the crimping step may create uniform spacing between the distal portions of the occlusion arms 440, 450 and the elongated biasing arms 120, 130. As will be discussed in more detail hereafter, the crimping step is operative to reshape the U-shaped recess 710 in order to retain portions of the fabric tube 376.

Subsequent to WEDM, each precursor clip (which all have the same shape and dimensions) is also subjected to a tissue engaging surface step. In exemplary form, the tissue engaging surface step machines away material from the occlusion arms 440, 450 (that previously had a block C-shaped profile; i.e. rectangular profile) to form the arcuate profile of the tissue engaging surfaces 480.

Further subsequent to WEDM, each precursor clip (which all have the same shape and dimensions) is subjected to a compression step. In exemplary form, the compression step establishes the dimension of any gap interposing the tissue engaging surface 480, as well as any preload exhibited by the clip 400. In this exemplary process, the precursor is compressed midway between the U-shaped section 110 and the distal ends 550 (by compressing the elongated biasing arms 120, 130), which causes the tissue engaging surfaces 480 to move toward one another. For example, the elongated biasing arms 120, 130 may be compressed approximately 0.38 inches, which results in zero gap between the tissue engaging surfaces 480 and a preload of approximately 1.5 pounds of force (i.e., 1.5 pounds of force or greater is required to separate the engaging surfaces 480 from one another). In other words, after the precursor is compressed, the exemplary clip 400 fabrication is complete and the clip components take on the preloaded positions shown in FIGS. 7-9.

Figure 11:
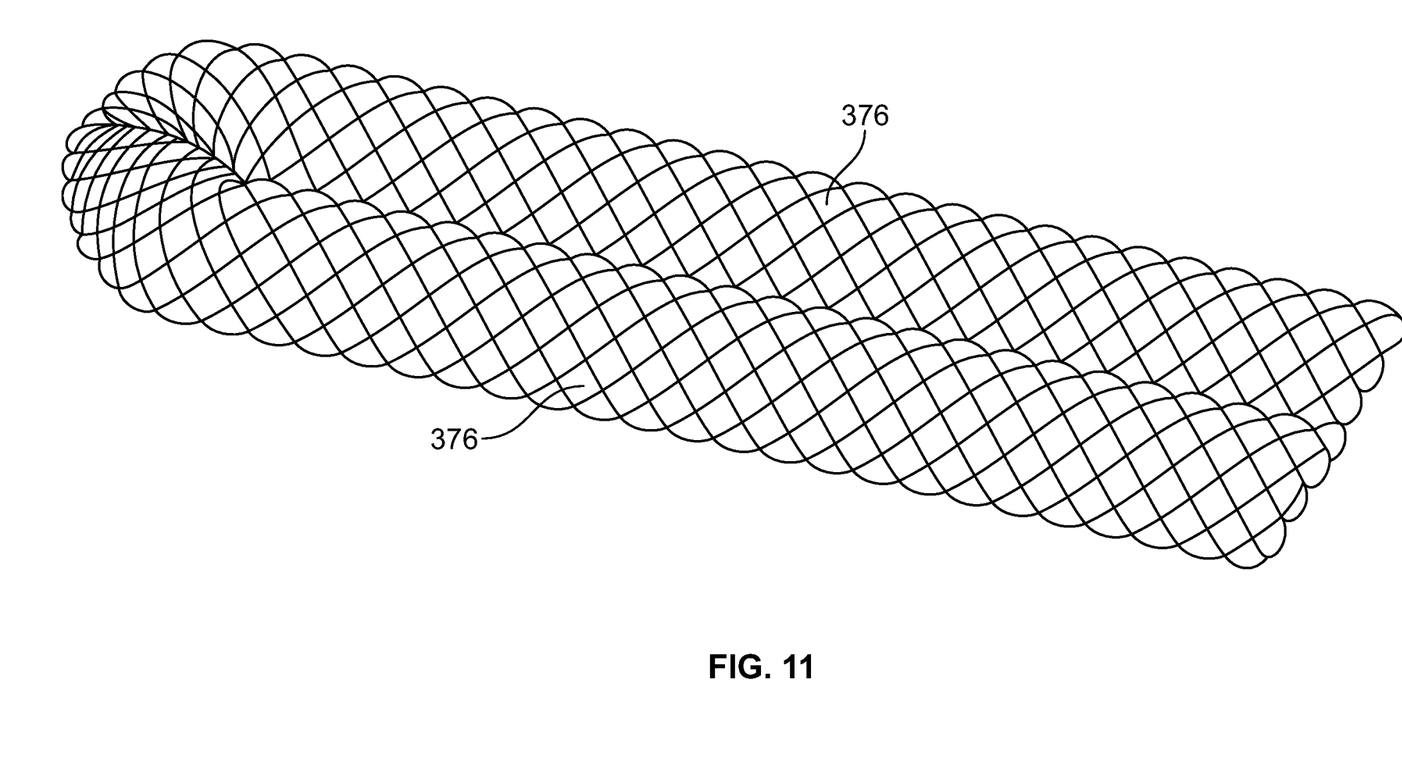
FIG. 11 is an elevated perspective view of the second exemplary occlusion clip of FIG. 7 shown in a closed position and covered by a fabric tube.

As shown in FIG. 11, in further exemplary form, the exemplary clip 400 may be encapsulated using a fabric tube 376 that may be fabricated from any of various materials operative to allow biologic tissue ingrowth such as, without limitation, polyethylene terephthalate and expanded polytetrafluoroethylene. In particular, the fabric tube 376 may be treated with collagen, albumin, etc., to promote tissue ingrowth. In this exemplary embodiment, a passage extends through the fabric tube, with opposing openings at the ends of the tube demarcating the beginning and end respectively of the passage. By way of example, one opening of the fabric tube 376 circumscribes one of the distal ends 550 of the clip 400 and is moved proximally along the length of the elongated biasing arm 120 and the elongated occlusion arm 440 to circumscribe both concurrently. Continued proximal movement of the fabric tube 376 eventually reaches the terminal end 460 of the elongated occlusion arm 440 and the U-shaped section 110, where the fabric tube follows the shape of the U-shaped section 110 and reaches the terminal end 460 of the elongated occlusion arm 450. At this point, the opening of the fabric tube 376 is repositioned distally to concurrently circumscribe the elongated biasing arm 130 and the elongated occlusion arm 450. Continued distal movement of the fabric tube 376 eventually results in the end of the fabric tube passing slightly beyond the distal end 550 of the elongated biasing arm 130 and the elongated occlusion arm 450, whereby the entire clip is housed within the passage of the fabric tube. The fabric tube 376 includes corresponding ends that extend beyond the distal ends 550 of the occlusion clip 100 a sufficient length to allow the corresponding ends to be tucked into the crimped U-shaped recess 710. The dimensions of each crimped U-shaped recess 710 are such that tucking a respective end of the fabric tube into each recess and thereafter crimping a distal portion of the U-shaped recess 710 (as discussed above pursuant to the crimping step) operates to retain the ends of the fabric tube within the U-shaped recess 710 via a friction fit. In this manner, contrary to the other exemplary embodiment, the ends of the fabric tube 376 are not sewn shut.

The foregoing exemplary fabric attachment may provide advantages over the other exemplary method that sews shut the fabric loop ends. By way of example, by securing the distal ends of the fabric to the distal ends of the clip 400, rotation of the fabric tube about the clip is retarded.

Following from the above description, it should be apparent to those of ordinary skill in the art that, while the methods and apparatuses herein described constitute exemplary embodiments of the present disclosure, the invention contained herein is not limited to these precise embodiments and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the claimed invention may exist even though they may not have been explicitly discussed herein.

What is claimed is:

1. A method of fabricating an occlusion clip comprising:
  cutting out an outline of an occlusion clip precursor from a sheet of material, the occlusion clip precursor including a pair of occlusion arms and a pair of biasing arms, where a respective gap separates each of the pair of occlusion arms from a respective one of the pair of biasing arms along a majority of a dominant longitudinal dimension of the occlusion clip; and,
  compressing the occlusion clip precursor to preload the pair of occlusion arms to form an occlusion clip.

2. The method of claim 1, further comprising submerging the sheet of material in a dielectric bath prior to cutting out the outline.

3. The method of claim 1, wherein cutting out the outline of the occlusion clip precursor from the sheet of material includes cutting the outline of a plurality of occlusion clip precursors from sheets of material, and further comprising submerging the sheets of material in a dielectric bath prior to cutting out the outline of the plurality of occlusion clip precursors.

4. The method of claim 1, wherein cutting out the outline of the occlusion clip precursor includes cutting out the outline of a first occlusion clip precursor from the sheet of material and cutting out the outline of a second occlusion clip precursor from the sheet of material, the first and second occlusion clip precursors having an identical shape, and the sheet of material is the same sheet of material.

5. The method of claim 1, wherein compressing the occlusion clip precursor includes setting a gap between each of the pair of occlusion arms and a respective one of the pair of biasing arms.

6. The method of claim 1, wherein the sheet of material comprises a metal having a thickness of approximately ⅛ inch.

7. The method of claim 1, wherein compressing the occlusion clip precursor establishes a preload of at least 1.12 pounds of force.

8. The method of claim 1, wherein compressing the occlusion clip precursor imparts a substantially constant closing force upon the pair of occlusion arms.

9. The method of claim 1, wherein the outline of the occlusion clip precursor includes at least three C-shapes lying along a common plane.

10. The method of claim 1, wherein the step of cutting out the outline is performed using electrical discharge machining.

11. The method of claim 10, wherein the electrical discharge machining includes wire electrical discharge machining.

12. The method of claim 1, further comprising wrapping the occlusion clip in a fabric.

13. The method of claim 12, wherein the fabric comprises a fabric tube that promotes tissue ingrowth.

14. The method of claim 1, wherein the occlusion clip comprises a continuous length of material interposing a pair of terminal ends, the continuous length of material including a first turn having a greater than 150 degree change of direction, a second turn having a greater than 150 degree change of direction, a third turn having a greater than 150 degree change of direction, where the third turn occurs at a proximal end of the occlusion clip, where the first and second turns occur proximate a distal end of the occlusion clip, where the proximal end and the distal end are opposite one another, and where the pair of terminal ends occur proximate the proximal end of the occlusion clip.

15. The method of claim 14, wherein compressing the occlusion clip precursor to preload the pair of occlusion arms includes preloading distal ends of the occlusion arms more heavily than proximal ends of the occlusion arms.

16. The method of claim 1, further comprising removing material from the occlusion clip precursor post cutting out the outline and prior to compressing the occlusion clip precursor.

17. The method of claim 16, wherein material is removed from the occlusion clip precursor to change a profile of a tissue engaging surface from a block C-shaped profile to an arcuate profile.

18. The method of claim 1, wherein compressing the occlusion clip precursor to preload the pair of occlusion arms imparts a non-uniform closing force across the pair of occlusion arms.

19. The method of claim 18, wherein compressing the occlusion clip precursor to preload the pair of occlusion arms and impart the non-uniform closing force includes preloading distal ends of the occlusion arms more heavily than proximal ends of the occlusion arms.

20. The method of claim 19, wherein preloading distal ends of the occlusion arms more heavily than proximal ends of the occlusion arms is operative to retard tissue clamped between the occlusion arms from squeezing out beyond the distal end when clamping tissue therebetween.

21. The method of claim 1, further comprising positioning a fabric tube over the pair of occlusion arms and the pair of biasing arms.

22. The method of claim 21, wherein at least a portion of the fabric tube concurrently circumscribes at least one of the pair of occlusion arms and at least one of the pair of biasing arms, in addition to a gap therebetween.

23. The method of claim 21, wherein repositioning the fabric tube over the pair of occlusion arms and the pair of biasing arms includes repositioning an end of the fabric tube within a recess of the occlusion clip and crimping the occlusion clip to secure the fabric tube within the recess.

24. The method of claim 21, wherein the fabric tube includes at least one open end prior to repositioning the fabric tube over the pair of occlusion arms and the pair of biasing arms, the method further comprising sewing the at least one open end closed subsequent to repositioning the fabric tube over the pair of occlusion arms and the pair of biasing arms.

* * * * *